(12) United States Patent
Miller et al.

(10) Patent No.: US 6,395,708 B1
(45) Date of Patent: *May 28, 2002

(54) METHOD FOR PREVENTING DIARRHEA

(75) Inventors: Langdon L. Miller, Lebanon; John David Rothermel, Randolph; Hugh Michael O'Dowd, Long Valley, all of NJ (US)

(73) Assignees: Novartis, A.G. (CH); Pharmacia & Upjohn Co. (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/648,270

(22) Filed: Aug. 25, 2000

Related U.S. Application Data

(63) Continuation of application No. 09/450,201, filed on Nov. 29, 1999, now Pat. No. 6,159,935.

(51) Int. Cl.$^7$ .......................... A61K 38/00; A61K 31/44
(52) U.S. Cl. ........................................ 514/12; 514/283
(58) Field of Search .................................. 514/12, 283

(56) References Cited

U.S. PATENT DOCUMENTS

| | | | |
|---|---|---|---|
| 4,395,403 A | 7/1983 | Bauer et al. | 424/177 |
| 4,473,692 A | 9/1984 | Miyasaka et al. | 546/48 |
| 4,604,463 A | 8/1986 | Miyasaka et al. | 544/125 |
| 5,786,344 A | 7/1998 | Ratain et al. | 514/100 |
| 5,789,411 A | 8/1998 | Gooberman et al. | |
| 5,876,761 A | 3/1999 | Bodmer et al. | |
| 5,919,760 A | 7/1999 | Simon | |
| 6,087,377 A * | 7/2000 | Ulrich | 514/324 |

FOREIGN PATENT DOCUMENTS

| | | |
|---|---|---|
| WO | WO 96/01127 | 1/1996 |
| WO | WO 98/37892 | 9/1998 |

OTHER PUBLICATIONS

Cascinu S., Curr. Opin. Oncol., Jul. 1995, vol. 7, (4), pp 325–9.
Lestingi TM et al., Proc. Annu. Meet. Am. Soc. Clin. Oncol., 14:A, 1563, 1995.
Kennedy P. et al., Proc. Am. Soc. Clin. Oncol., 9:324, 1990.
Cascinu S. et al., Eur. J. Cancer, 1992, 28:482–483.
Petrelli N. et al., Cancer 1993, 75:1543–1546.
Wadler et al., J. Clin. Oncol., 13(1):222–6, Jan. 1995.
Cascinu S. et al., Oncology 1994, 51:70–73.
Meropol NJ et al., Am. J. Clin. Oncol., 21(2):135–8, 1998.
Cunningham et al., Lancet vol. 352 (9138) Oct. 31, 1998, 1413–1418.
Takasuna et al., Cancer Research, 1996, 56:3752–3757.
Cascinu S. et al., Journal of Clinical Oncology, 1993, vol. 11, No. 1, 148–151.
Takasuna et al., Jpn. J. Cancer Res., 1995, 86:978–984.
Rougier et al., Seminars in Oncology, 1996, vol. 23, No. 1 (Suppl 3), 34–41.
Sakata et al., Gan To Kagaku Ryoho, 1994, vol. 21, 1241–1244.
D. Berg, "Managing the side effects of chemotherapy for colorectal cancer", Seminars in Oncology, 1998, 25/5 Supp,. pp. 53–59.
J.R. Hecht, "Gastrointestinal irinotecan", Oncology, 1998, 12/8 Suppl., pp. 72–78.
V.M.M. Herben et al., "Phase I and pharmacokinetic study of irinotecan administered as a low–dose, continuous intravenous infusion over 14 days in patients with malignant solid tumors", Journal of Clinical Oncology, 1999, 17/6, pp. 1897–1905.

* cited by examiner

*Primary Examiner*—Theodore J. Criares
*Assistant Examiner*—Jennifer Kim
(74) *Attorney, Agent, or Firm*—McDonnell Boehnen Hulbert & Berghoff

(57) ABSTRACT

The present invention relates to a method for preventing irinotecan-induced or camptothecin-induced or camptothecin- analog-induced diarrhea by administering an effective amount of octreotide. In particular the invention concerns new methods, combination formulations and kits to prevent late diarrhea caused by irinotecan or camptothecin, or camptothecin-analog administration.

2 Claims, No Drawings

METHOD FOR PREVENTING DIARRHEA

This is a continuation divisioinal continuation-in-part of application Ser. No. 09/450,201 filed on Nov. 29, 1999, now U.S. Pat. No. 6,159,935 entitled Method for Preventing Diarrhea.

TECHNICAL FIELD OF THE INVENTION

The present invention relates to an agent for preventing diarrhea and particularly to a pharmaceutical agent for preventing diarrheal symptoms caused by administration of irinotecan or a salt thereof, particularly in the form of its hydrochloride, or attributed to its active metabolite, SN-38. More particularly, the invention concerns new methods, combination formulations and kits to prevent late diarrhea induced by irinotecan administration.

In the present specification, unless otherwise specified, the term "irinotecan" includes also pharmaceutically acceptable salts, e.g., the hydrochloride salt, and metabolites, such as, e.g. SN-38. In the present specification, unless otherwise specified, the term "octreotide" includes also pharmaceutically acceptable salts of octreotide, e.g., the acetate. By the term "administered" or "administering" as used herein, is meant standard delivery methods, e.g., parenteral administration, including continuous infusion and intravenous, intramuscular and subcutaneous injections, and oral administration.

BACKGROUND OF THE INVENTION

Diarrhea, characterized by the frequent defecation of liquid or liquid-like stools, often develops as a side effect during clinical treatment with chemotherapeutic agents. This adverse effect is most commonly associated with chemotherapeutic agents such as 5-fluorouracil, cisplatin or irinotecan hydrochloride. In particular, late diarrhea due to the administration of irinotecan can be prolonged, may lead to dehydration and electrolyte imbalance and can be, in some cases, sufficiently serious that irinotecan administration must be modified, interrupted or discontinued. Diarrhea poses a problematic symptom for patients, and because it may provoke reductions in irinotecan doses or the frequency of irinotecan administration, diarrhea may compromise the therapeutic efficacy of irinotecan.

While there is a substantial need for development of an agent for preventing diarrhea, particularly late diarrhea caused by irinotecan, no definite and efficacious method for preventing irinotecan-induced diarrhea has been identified. It is therefore an object of the present invention to provide an agent for preventing diarrhea, in particular late diarrhea, induced by irinotecan administration.

SUMMARY OF THE INVENTION

The present invention provides a method for preventing diarrhea caused by the administration of irinotecan. The invention comprises administration of octreotide or a pharmaceutically acceptable salt thereof, in particular octreotide acetate, to patients receiving irinotecan. Optionally, octreotide or a pharmaceutically acceptable salt thereof can be administered together with an anticholinergic agent, e.g., atropine, and/or with one or more antiemetic agents, e.g., dexamethasone, ondansetron or granisetron. Octreotide or a pharmaceutically acceptable salt thereof may be administered simultaneously with irinotecan, or the compounds may be administered sequentially, in any desirable order. Preferably, octreotide is administered before or concurrent with administration of irinotecan.

The present invention is also directed to combining separate pharmaceutical compositions containing irinotecan or, respectively, octreotide or its salts in kit form.

DETAILED DESCRIPTION OF THE INVENTION

The present invention provides a method for preventing diarrhea caused by the administration of irinotecan. The invention comprises administration of octreotide to patients receiving irinotecan-containing therapy.

The preparation and use of irinotecan is known (see U.S. Pat. No. 4,604,463). It is available commercially in the form of CAMPTOSAR™ Injection, sold, e.g., by Pharmacia & Upjohn; and as CAMPTO™, sold by Rhone-Poulenc Rorer.

The preparation and use of SN-38 (10-ethyl 7-hydroxy camptothecin) is known (see U.S. Pat. No. 4,473,692). The preparation and use of octreotide is also well known (see U.S. Pat. No. 4,395,403). This is commercially available as the active ingredient in SANDOSTATIN™ and SANDOSTATIN LAR™ Depot, sold by Novartis.

Irinotecan is (4S)-4,11-diethyl-4-hydroxy-9-[(4-piperidino-piperidino)carbonyloxy]-1H-pyrano[3',4'.6,7]indolizino [1,2-b]quinoline-3,14(4H,12H)dione. Irinotecan hydrochloride is a pale yellow to yellow crystalline powder, with the empirical formula $C_{33}H_{38}N_4O_6HCl3H_2O$ and a molecular weight of 677.19. Irinotecan hydrochloride was clinically investigated as CPT-11. Irinotecan is a prodrug converted in vivo by plasma and tissue carboxylesterases to SN-38 (7-ethyl-10-hydroxy camptothecin), an active metabolite that is an inhibitor of the nuclear enzyme topoisomerase I. Irinotecan has shown activity against a variety of tumor types, and in particular, refractory colorectal tumors.

Late-onset diarrhea, a severe delayed chronic grade 3–4 diarrhea, generally occurring more than 8 hours after administration of irinotecan, is the major dose-limiting toxicity in cancer patients receiving irinotecan therapy. The loss of fluids and electrolytes associated with late diarrhea can result in life-threatening dehydration, renal insufficiency, and electrolyte imbalances. The life-threatening aspects of persistent or severe diarrhea can require aggressive treatment and may lead to hospitalization. Persistent and severe diarrhea can also have negative effect on the patient's quality of life, and interferes with roles and responsibilities and interpersonal relationships and promotes feelings of social isolation. Because it may provoke reductions in irinotecan doses or the frequency of irinotecan administration, diarrhea may also compromise the therapeutic efficacy of irinotecan.

Quick resolution or, more preferably, prevention of late diarrhea is important, not only to prevent hospitalization, but also to improve quality of life and to enable patients to continue chemotherapy treatment at adequate doses in order to obtain the best antitumor effect. A variety of strategies for the control of chemotherapeutic-related diarrhea, particularly for the control of diarrhea induced by irinotecan, have been examined in humans and in animal models.

In humans, intensive, immediate application of loperamide (an agent that slows intestinal motility and affects water and electrolyte movement through the bowel) has been used to reduce or control diarrhea once diarrhea has started (Rougier P, Bugat R. CPT-11 in the treatment of colorectal cancer: clinical efficacy and safety profile. Semin Oncol 1996;23(Suppl 3): 34–41.) Though often successful in reducing the severity of diarrhea, this agent had not reduced the frequency of diarrhea, requires administration at 2-hour intervals following the onset of diarrhea, and is not used prophylactically.

The Chinese herbal medicine, kampo, has also been shown to control diarrhea in rats and humans; baicalin, one component of kampo, has similar activity (see, e.g., Takasuna K, Kasai Y, Kitano Y, Mori K, Kobayashi R, Hagiwara T, Kakihata K, Hirohashi M, Nomura M, Nagai E, et al. Protective effects of kampo medicines and baicalin against intestinal toxicity of a new anticancer camptothecin derivative, irinotecan hydrochloride (CPT-11), in rats. Jpn J. Cancer Res. 1995;86:978–984; and, Sakata Y, Suzuki H, Kamataki T. Preventive effect of TJ 14, a kampo (Chinese herb) medicine, on diarrhea induced by irinotecan hydrochloride (CPT-11), Gan To Kagaku Ryoho 1994; 21:1241–1244.) Though the mechanism is not clearly defined, the anti-diarrheal activity of kampo or baicalin is thought to be through inhibition of beta glucuronidases in the gastrointestinal tract. This enzyme is responsible for the deconjugation of the glucuronide form of the active irinotecan metabolite, SN-38. Deconjugation of the SN-38 glucuronide is thought to release active SN-38 back into the intestinal lumen and produce toxic effects on the intestinal epithelium.

Since most of the intestinal beta-glucuronidase activity is due to microbial flora, antibiotics have also been suggested to have protective effects (Takasuna K, Hagiwara T, Hirohashi M, Kato M, Nomura M, Nagai E, Yokoi T, Kamatake T. Involvement of beta-glucuronidase in intestinal microflora in the intestinal toxicity of the antitumor camptothecin derivative irinotecan hydrochloride (CPT-11) in rats. Cancer Res 1996;56:3752–3757), again through reduction of beta-glucuronidase activity.

While potentially useful, the effects of kampo medicines or other beta-glucuronidase inhibitors on SN-38 pharmacokinetics or irinotecan efficacy are not presently known. It is possible that such drugs would alter the pharmacology of irinotecan and/or SN-38 sufficiently to reduce the efficacy of the drug in treating cancer. It is also not clear what contribution intraluminal exposure to irinotecan or SN-38 makes relative to mesenteric artery exposure in inducing irinotecan-mediated late diarrhea.

Another experimental co-therapy for ameliorating delayed diarrhea is octreotide (Cascinu S. Management of diarrhea induced by tumors or cancer therapy. Curr. Opin. Oncol. 1995;7:325–329). In 1990, Kennedy et al. reported encouraging results of treatment with octreotide in 11 patients with colorectal cancer suffering from diarrhea after chemotherapy with 5-fluorouracil (Proc. Am. Soc. Clin. Oncol., 1990 9:324). These data were confirmed in other pilot trials (Cascinu S. et al., Eur. J. Cancer, 1992 28–482–483; and Petrelli N. et al., Cancer 1993, 75–1543–1546) and in a randomized trial comparing octreotide with loperamide in the therapy of 5-fluorouracil-induced diarrhea, in which octreotide was shown to be more effective than loperamide and probably more cost-effective (Cascinu S. et al., J. Clin. Oncol., 1993, 11:148–151). Octreotide has been found to be active in preventing diarrhea associated with the administration of cisplatin in patients who experienced this side-effect during a previous course of chemotherapy (Cascinu S., Fedeli A., Luzi Fedeli S. and Catalano G., Oncology, 1994;51:70–73). Conversely, a study undertaken to determine whether octreotide could be used as prophylaxis against chemotherapy-induced diarrhea, revealed that octreotide does not prevent diarrhea associated with 5-fluorouracil plus leucovorin although octreotide was successful in the treatment of 5-fluorouracil-induced diarrhea (Meropol N. J, Blubenson L. E. and Creaven P. J., Am. J. Clin. Oncol., 21(2):135–138, 1998).

In summary, while octreotide appears to be effective in treating chemotherapy-induced diarrhea once it occurs, conflicting data are reported in the closest prior art with regard to the efficacy of octreotide in preventing diarrhea induced by chemotherapeutic drugs such as cisplatin and 5-fluorouracil, known to cause severe forms of diarrhea. Nothing is reported in the art about the use of octreotide in the prophylaxis of irinotecan-induced diarrhea.

This means that the efficacy of octreotide in preventing diarrhea induced by antitumor drugs needs to be explored on a case-by-case basis, and cannot be predicted by making reference to prior-art documents.

The present situation is such that there is not yet any efficacious and safe agent, which is suitable in the prophylaxis of diarrhea, particularly late diarrhea, induced by irinotecan administration to a cancer patient.

The present invention provides a method for preventing diarrhea caused by the administration of irinotecan and comprises administration of octreotide to patients receiving irinotecan alone or irinotecan in combination with other antineoplastic agents. In preventing diarrheal symptoms in patients receiving irinotecan-containing therapy, octreotide has the potential to reduce the incidence, severity, and/or duration of diarrhea; improve patient quality of life; avoid hospitalization; and/or prevent irinotecan dose reduction, interruption, or discontinuation.

Octreotide is known chemically as L-cysteinamide,D-phenylalanyl-L-cysteinyl-L-phenylalanyl-D-tryptophyl-L-lysyl-L-threonyl-N-[2-hydro-1-hydroxymethyl) propyl]-, cyclic (2→7)-disulfide; [R-(R*,R*)]. It is an octapeptide with pharmacologic properties mimicking those of the natural hormone somatostatin. Octreotide acetate, the acetate salt of the above-defined cyclic octapeptide, is the preferred agent according to this invention. In a further preferred embodiment, octreotide acetate, formulated in a long-acting slow-release dosage form, is administered to prevent diarrhea caused by irinotecan administration. Octreotide acetate long-acting release formulation, commercially available as SANDOSTATIN LAR™ Depot, is a dosage form consisting of microspheres of the biodegradable glucose star poly D, L-lactic and glycolic acids copolymer, containing octreotide acetate. It maintains all of the clinical and pharmacological characteristics of the immediate-release dosage form, Sandostatin™ (octreotide acetate) injection, with the added feature of slow release of octreotide from the site of injection, reducing the need for frequent administration. This slow release occurs as the polymer biodegrades, primarily through hydrolysis. It is currently recommended that Sandostatin LAR™ Depot be injected intramuscularly (intragluteally) once every four weeks.

In the prophylaxis of diarrhea according to the invention, octreotide may be administered simultaneously with irinotecan, or the compounds may be administered sequentially, in any desired order. Preferably octreotide is administered some days before the first irinotecan administration and subsequent octreotide administrations are before or simultaneous with irinotecan administration, the time of administration (dosing intervals) of octreotide depending on the preferred irinotecan-scheduled regimen.

In a preferred embodiment of the present invention, octreotide acetate long-acting release formulation is administered 10–14 days prior to the first irinotecan dose. For example, when irinotecan is administered in a planned 6-week cycle, wherein irinotecan is given intravenously as a single-agent or in combination with other antineoplastic agents such as, e.g., cisplatin, 5-fluoruracil or others, over 30–90 minutes once weekly for 4 weeks followed by a 2-week rest period, octreotide acetate long-acting release formulation may be administered prior to the first irinotecan dose and again on Day 15 or Day 22 of this 6-week cycle. The octreotide acetate long-acting release formulation dosage is 10 mg, 20 mg or 30 mg at the time of each octreotide administration.

Alternatively, when irinotecan is administered using an every-2-week or every-3-week regimen, wherein irinotecan is given intravenously as a single-agent or in combination with other antineoplastic agents, such as, e.g., cisplatin, 5-fluoruracil, or others, over 30–90 minutes once every 2 or 3 weeks, octreotide acetate long-acting release formulation may be administered prior to the first irinotecan dose, e.g., from 10 to 14 days before the first irinotecan dose and then approximately every further 2 or 3 weeks, just before or concurrent with the commencement of a further 2-week or 3-week cycle of irinotecan administration. The octreotide acetate long-acting release formulation dosage is 10 mg, 20 mg or 30 mg at the time of each octreotide administration.

It has been found that this octreotide prophylactic treatment avoids or remarkably limits the severity and duration of diarrhea in many cases. Without such prophylactic treatment, patients suffer more frequent, more severe, or more prolonged discomfort due to diarrhea; and/or have reductions in dose and/or frequency of administration of irinotecan-containing therapy; and/or experience a lesser quality of life.

Beyond prevention of late diarrhea with octreotide, its use may be optionally associated with the prevention and/or therapy of other side effects commonly associated with irinotecan administration, e.g., cholinergic syndrome and nausea and/or vomiting. Nausea and/or vomiting can occur on the day of irinotecan administration and prolonged nausea and/or vomiting can occur for several days afterwards. To prevent nausea and vomiting on the day of admninistration, one or more antiemetics, for example dexarnethasone (DECADRON™) alone or dexamethasone plus another antiemetic of choice, can be given before the treatment is initiated. In addition to dexamethasone or as an alternative to dexamethasone, patients may be premedicated with a serotononin antagonist, e.g., ondansetron (ZOFRAN™), granisetron (KITRYL™) or dolasetron mesylate (ANZEMET™). Prochloperazine (COMPAZINE™) or similar oral anti-emetics may be recommended for prolonged nausea.

Lacrimation, meiosis, rhinorrhea, nasal congestion, diaphoresis, flushing, bradycardia, abdominal cramping and/or early-onset diarrhea may also occur during or up to 24 hours after receiving irinotecan. The constellation of early symptoms are consistent with cholinergic hyperstimulation and can be treated with anticholinergic agents e.g., atropine. Most commonly administered is atropine in a dosage usually ranging from about 0.25 mg to about 1 mg intravenously or subcutaneously.

A single pharmaceutical composition that comprises both octreotide and irinotecan may be employed for simultaneously administration, or separate pharmaceutical compositions, each containing only one active ingredient, may also be used. If desired, where an anticholinergic agent and/or an antiemetic agent is used, a combined therapeutic cocktail may be prepared and administered to a patient.

It is therefore a further object of the present invention to provide a pharmaceutical composition comprising a pharmaceutically acceptable carrier or excipient and, as an active ingredient, irinotecan and octreotide, and optionally, an antiemetic and/or an anti-cholinergic agent. Pharmaceutically acceptable carriers or excipients to be utilized in the preparation of a pharmaceutical composition according to the invention are well known to people skilled in the art of formulating compounds in the form of pharmaceutical compositions. Such pharmaceutical compositions may routinely contain pharmaceutically acceptable salts, buffering agents, preservatives and/or compatible carriers. As used herein "pharmaceutically acceptable carrier" refers to one or more compatible solid or liquid fillers, diluents or encapsulating substances that are suitable for administration to mammals including humans.

Since the present invention relates to the prevention of irinotecan-induced diarrhea or other symptoms by treatment with a combination of active ingredients wherein said active ingredients may be administered separately, the invention also relates to combining separate pharmaceutical compositions in kit form. That is, a kit is contemplated wherein two or more separate units are combined: an irinotecan pharmaceutical composition, an octreotide pharmaceutical composition, and optionally also an antiemetic and/or anticholinergic composition.

It is therefore a further object of the present invention a kit comprising a package housing a first container containing a pharmaceutical composition comprising irinotecan and a second container containing a pharmaceutical composition comprising octreotide. A kit as described above, which further comprises a third container containing a pharmaceutical composition comprising an anticholinergic agent or an antiementic agent, is also an object of the invention. A kit comprising a package housing a first container containing a pharmaceutical composition comprising irinotecan, a second container containing a pharmaceutical composition comprising octreotide, a third container containing a pharmaceutical composition comprising an anticholinergic agent and a forth container containing a pharmaceutical composition comprising an antiemetic agent is also contemplated in the present invention. The kit will preferably include directions for the administration of the separate components. The kit form is particularly advantageous when the separate components must be administered in different dosage forms (e.g. oral and parenteral) or are administered at different dosage intervals.

It will be appreciated that the actual preferred method and order of administration will vary according to, inter alia, the particular formulation of irinotecan, the particular formulation of octreotide being utilized, the particular formulation of an antiemetic and/or anticholinergic agent, the particular tumor being treated and the particular patient being treated. The dosage ranges for the administration of the combined preparation may vary with the age, condition, sex and extent of the disease in the patient and can be determined by someone of skill in the art. The dosage regimens must therefore be tailored to the particular of the patient's condition, response to therapy and associated treatments in a manner which is conventional for any therapy, and may need to be adjusted in response to changes in conditions and/or in light of other clinical situations.

The present invention is also concerned with the use of octreotide for the prevention of diarrhea induced by any camptothecin or camptothecin analog including camptothecin derivatives other than irinotecan. Examples of such camptothecin derivatives are SN-22,9-amino-camptothecin, 9-nitro-camptothecin (rubitecan) and topotecan. Cancer treatment with these derivatives may be successfully accompanied with octreotide treatment at suitable dosages and administration schedules, which may be similar to those reported above for the case of anticancer treatment with irinotecan.

The present disclosure is an exemplification of the principles of the invention and is not intended to limit the invention to the particular embodiments illustrated. Those skilled in the art may recognize other equivalents to the specific embodiment described herein which equivalents are intended to be encompassed by the claims attached hereto.

What is claimed is:

1. A method for preventing diarrhea caused by the administration of irinotecan or a pharmaceutically acceptable salt or metabolite thereof, which comprises administering a pharmaceutical composition comprising a pharmaceutically acceptable carrier or excipient and, as active ingredients, a therapeutically effective amount of irinotecan or a pharmaceutically acceptable salt or metabolite thereof and a therapeutically effective amount of octreotide or a pharmaceutically acceptable salt thereof.

2. A method for preventing diarrhea caused by the administration of any camptothecin or camptothecin analog or a pharmaceutically acceptable salt or metabolite thereof, which comprises administering a pharmaceutical composition comprising a pharmaceutically acceptable carrier or excipient and, as active ingredients, a therapeutically effective amount of any camptothecin or camptothecin analog or a pharmaceutically acceptable salt or metabolite thereof and a therapeutically effective amount of octreotide or a pharmaceutically acceptable salt thereof.

* * * * *